(12) United States Patent
Heckroth et al.

(10) Patent No.: US 10,391,198 B2
(45) Date of Patent: *Aug. 27, 2019

(54) MEDICAL ADHESIVES FOR STOPPING HEAVY BLEEDING AND SEALING LEAKAGES

(71) Applicant: Adhesys Medical GmbH, Aachen (DE)

(72) Inventors: Heike Heckroth, Odenthal (DE); Burkhard Köhler, Zierenberg (DE); Sebastian Dörr, Düsseldorf (DE)

(73) Assignee: Adhesys Medical GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/148,272

(22) Filed: Oct. 1, 2018

(65) Prior Publication Data

US 2019/0030206 A1    Jan. 31, 2019

Related U.S. Application Data

(63) Continuation of application No. 15/667,744, filed on Aug. 3, 2017, now Pat. No. 10,117,963, which is a continuation of application No. 13/054,673, filed as application No. PCT/EP2009/004833 on Jul. 4, 2009, now Pat. No. 9,764,058.

(30) Foreign Application Priority Data

Jul. 17, 2008  (EP) .................................. 08012901

(51) Int. Cl.
| | |
|---|---|
| *A61L 24/00* | (2006.01) |
| *A61L 24/04* | (2006.01) |
| *C08G 18/08* | (2006.01) |
| *C08G 18/10* | (2006.01) |
| *C08G 18/38* | (2006.01) |
| *C09J 175/12* | (2006.01) |
| *C08L 75/04* | (2006.01) |
| *C08G 18/48* | (2006.01) |

(52) U.S. Cl.
CPC ......... *A61L 24/0094* (2013.01); *A61L 24/046* (2013.01); *C08G 18/089* (2013.01); *C08G 18/10* (2013.01); *C08G 18/4837* (2013.01); *C08L 75/04* (2013.01); *C09J 175/12* (2013.01); *A61L 2400/04* (2013.01)

(58) Field of Classification Search
CPC .............. A61L 24/0094; A61L 24/046; A61L 2400/04; C08G 18/089; C08G 18/10; C08G 18/4837; C08L 75/04; C09J 175/12
See application file for complete search history.

(56) References Cited

U.S. PATENT DOCUMENTS

| | | | |
|---|---|---|---|
| 4,740,534 A | 4/1988 | Matsuda et al. | |
| 5,126,170 A | 6/1992 | Zwiener et al. | |
| 5,243,012 A | 9/1993 | Wicks et al. | |
| 7,754,782 B2 | 7/2010 | Heckroth et al. | |
| 9,000,089 B2 | 4/2015 | Heckroth et al. | |
| 9,051,410 B2 | 6/2015 | Heckroth et al. | |
| 9,404,026 B2 | 8/2016 | Heckroth et al. | |
| 9,421,298 B2 | 8/2016 | Heckroth et al. | |
| 9,764,058 B2 * | 9/2017 | Heckroth et al. | |
| 10,117,963 B2 * | 11/2018 | Heckroth et al. | |
| 2004/0067315 A1 | 4/2004 | Niesten et al. | |
| 2005/0129733 A1 | 6/2005 | Milbocker et al. | |
| 2007/0248567 A1 | 10/2007 | Pathak et al. | |

FOREIGN PATENT DOCUMENTS

| | | |
|---|---|---|
| DE | 69311633 T2 | 10/1997 |
| EP | 1081171 A2 | 3/2001 |
| EP | 1719530 A2 | 11/2006 |

\* cited by examiner

*Primary Examiner* — Alma Pipic
(74) *Attorney, Agent, or Firm* — Drinker Biddle & Reath LLP

(57) ABSTRACT

The present invention relates to a method that includes providing a formulation having an isocyanate-functional prepolymer and a curing component comprising an amino-functional aspartic ester of the general formula (I)

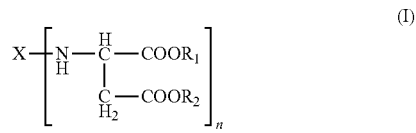

applying the formulation to a cell tissue; and curing the formulation such that the loss of blood (haemostatic) or tissue fluids is staunched or leaks in cell tissues are sealed.

12 Claims, No Drawings

MEDICAL ADHESIVES FOR STOPPING HEAVY BLEEDING AND SEALING LEAKAGES

CROSS-REFERENCE TO RELATED APPLICATIONS

This application is a continuation application of U.S. patent application Ser. No. 15/667,744, filed Aug. 3, 2017, which is a continuation of U.S. patent application Ser. No. 13/054,673, filed Jan. 18, 2011, which is a national stage application (under 35 U.S.C. § 371) of PCT/EP2009/004833, filed Jul. 4, 2009, which claims benefit of European application 08012901.87, filed Jul. 17, 2008.

BACKGROUND OF THE INVENTION

The present invention relates to innovative, quick-curing adhesives based on hydrophilic polyisocyanate prepolymers and intended for use in emergency care for staunching severe bleeding (haemorrhage) and sealing leaks.

A variety of materials used as tissue adhesives are available commercially. They include the cyanoacrylates Dermabond® (octyl 2-cyanoacrylate) and Histoacryl Blue® (butyl cyanoacrylate). A requirement for efficient bonding of the cyanoacrylates are dry substrates. In cases of severe bleeding the adhesive fails.

As an alternative to the cyanoacrylates there are biological adhesives available such as, for example, BioGlue®, a mixture of glutaraldehyde and bovine serum albumen, a variety of collagen- and gelatine-based systems (FloSeal®) and also the fibrin adhesives (Tissucol). These systems serve primarily for haemostasis (stopping bleeding). Apart from the high costs, fibrin adhesives are notable for a relatively weak adhesion and a rapid breakdown, and so can be used only in cases of relatively minor injury on unstretched tissue. Collagen- and gelatine-based systems such as FloSeal® serve exclusively for haemostasis. Moreover, because fibrin and thrombin are obtained from human material, and collagen and gelatine from animal material, there is always a risk of infection in biological systems. Furthermore, biological materials must be given refrigerated storage, and so their use in emergency care such as in disaster zones, for example, or in the case of military deployment, etc., is not possible. In these cases there are QuikClot® or QuikClot ACS+™ available to treat traumatic wounds, QuikClot being a granular mineral which in an emergency is inserted into the wound, where it leads to coagulation as a result of removal of water. In the case of QuikClot® this is a highly exothermic reaction, leading to burns. QuikClot ACS+™ is a gauze into which the salt has been embedded. For haemostasis the system must be pressed firmly onto the wound.

The possible application of polyurethane prepolymers as a haemostatic is addressed in the articles "Isocyanate-terminated urethane prepolymer as bioadhesive material: evaluation of bioadhesion and biocompatibility, in vitro and in vivo assays" (Journal of Biomaterials Science, Polymer Edition (2001), 12(7), 707-719) and "Development of a biodegradable bioadhesive containing urethane groups" (Journal of Materials Science: Materials in Medicine (2008), 19(1), 111-120).

It has now been found that formulations comprising specific hydrophilic polyurethane prepolymers and amino-functional curing agents can be used with outstanding effect as a haemostatic for stopping blood. In addition, the formulations have an advantageous adhesive quality, and so, as well as stopping blood, the effect is achieved at the same time of the fixing of the film formed by the formulation on the injury site. Furthermore, by this means, particularly in the case of relatively severe injury, sections of tissue can be joined to one another again and fixed, which is advantageous for the would healing process.

BRIEF DESCRIPTION OF THE INVENTION

The present invention accordingly provides for the use of formulations comprising
A) isocyanate-functional prepolymers obtainable from
 A1) aliphatic isocyanates and
 A2) polyols having number-average molecular weights of >400 g/mol and average OH functionalities of 2 to 6,
B) a curing component comprising
 B1) amino-functional aspartic esters of the general formula (I)

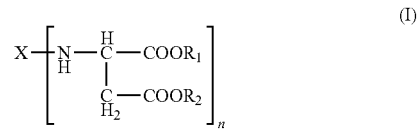

where
X is an n-valent organic radical obtained by removing the primary amino groups of an n-functional amine,
$R_1$ and $R_2$ are identical or different organic radicals which contain no Zerewitinoff-active hydrogen and
n is an integer of at least 2
and
 B2) optionally, organic fillers which have a viscosity as measured to DIN 53019 at 23° C. in the range from 10 to 6000 mPas
and
C) optionally, reaction products of isocyanate-functional prepolymers as defined for component A) with aspartic esters as per component B1) and/or organic fillers as .per component B2)
to staunch the loss of blood (haemostatic) or tissue fluids or to seal leakages in cell tissues.

Likewise provided by the present invention is the use of aforementioned formulations for producing a composition for staunching the loss of blood (haemostatic) or tissue fluids or for sealing leaks in cell tissues.

Likewise provided by the invention is a method of staunching the loss of blood (haemostatic) or tissue fluids or for sealing leaks in cell tissues, by applying the formulations that are essential to the invention to a cell tissue and then curing them.

DETAILED DESCRIPTION OF THE INVENTION

The staunching, essential to the invention, of the loss of fluid or blood or the sealing of leaks in cell tissues can be carried out both in vivo and in vitro.

For the definition of Zerewitinoff-active hydrogen, refer to Rompp Chemie Lexikon, Georg Thieme Verlag Stuttgart. Groups with Zerewitinoff-active hydrogen comprehend, preferably, OH, NH or SH.

Tissue or cell tissue is understood in the context of the present invention to refer to associations of cells which consist of cells of the same form and function, such as surface tissue (skin), epithelial tissue, myocardial, connective or stromal tissue, muscles, nerves and cartilage. This also includes, among other systems, all organs made up of associations of cells, such as the liver, kidneys, lungs, heart, etc.

The isocyanate-functional prepolymers used in A) are obtainable by reacting isocyanates with hydroxyl-functional polyols, with the optional addition of catalysts and also auxiliaries and additives.

Examples of isocyanates which can be used in A1) include monomeric aliphatic or cycloaliphatic di- or triisocyanates such as 1,4-butylene diisocyanate (BDI), 1,6-hexamethylene diisocyanate (HDI), isophorone diisocyanate (IPDI), 2,2,4- and/or 2,4,4-trimethylhexamethylene diisocyanate, the isomeric bis(4,4'-isocyanatocyclohexyl)methanes or their mixtures of any desired isomer content, 1,4-cyclohexylene diisocyanate, 4-isocyanatomethyl-1,8-octane diisocyanate (nonane triisocyanate), and also alkyl 2,6-diisocyanatohexanoates (lysine diisocyanate) with C1-C8 alkyl groups.

Besides the abovementioned monomeric isocyanates it is also possible to use their higher molecular mass derivatives with uretdione, isocyanurate, urethane, allophanate, biuret, iminooxadiazinedione or oxadiazinetrione structure and also mixtures thereof.

In A1) it is preferred to use isocyanates of the aforementioned kind having exclusively aliphatically or cycloaliphatically attached isocyanate groups or mixtures thereof.

The isocyanates or isocyanate mixtures used in A1) preferably have an average NCO functionality of 2 to 4, more preferably 2 to 2.6 and very preferably 2 to 2.4.

In one particularly preferred embodiment hexamethylene diisocyanate is used in A1).

For the synthesis of the prepolymer in A2) it is possible in principle to use all of the polyhydroxy compounds known per se to the skilled person that have 2 or more OH functions per molecule. These may be, for example, polyester polyols, polyacrylate polyols, polyurethane polyols, polycarbonate polyols, polyether polyols, polyester polyacrylate polyols, polyurethane polyacrylate polyols, polyurethane polyester polyols, polyurethane polyether polyols, polyurethane polycarbonate polyols, polyester polycarbonate polyols or any desired mixtures thereof with one another.

The polyols used in A2) preferably have an average OH functionality of 3 to 4.

The polyols used in A2) further preferably have a number-average molecular weight of 400 to 20 000 g/mol, more preferably 2000 to 10 000 g/mol and very preferably 4000 to 8500.

Polyether polyols are preferably polyalkylene oxide polyethers based on ethylene oxide and optionally propylene oxide.

These polyether polyols are based preferably on starter molecules with a functionality of two or more, such as difunctional or higher polyfunctional alcohols or amines.

Examples of such starters are water (considered to be a diol), ethylene glycol, propylene glycol, butylene glycol, glycerol, TMP, sorbitol, pentaerythritol, triethanolamine, ammonia or ethylenediamine.

Preferred polyalkylene oxide polyethers correspond to those of the aforementioned kind and contain from 50% to 100%, preferably 60% to 90%, of ethylene oxide-based units, based on the amounts of alkylene oxide units that are present in total.

Preferred polyester polyols are the polycondensates—known per se—of diols and also, optionally, triols and tetraols and of dicarboxylic and also, optionally, tricarboxylic and tetracarboxylic acids or hydroxycarboxylic acids or lactones. In place of the free polycarboxylic acids it is also possible to use the corresponding polycarboxylic anhydrides or corresponding polycarboxylic esters of lower alcohols for preparing the polyesters.

Examples of suitable diols are ethylene glycol, butylene glycol, diethylene glycol, triethylene glycol, polyalkylene glycols such as polyethylene glycol, and also 1,2-propanediol, 1,3-propanediol, butane-1,3-diol, butane-1,4-diol, hexane-1,6-diol and isomers, neopentyl glycol or neopentyl glycol hydroxypivalate, preference being given to hexane-1,6-diol and isomers, butane-1,4-diol, neopentyl glycol and neopentyl glycol hydroxypivalate. In addition it is also possible to use polyols such as trimethylolpropane, glycerol, erythritol, pentaerythritol, trimethylolbenzene or trishydroxyethyl isocyanurate.

As dicarboxylic acids it is possible to use phthalic acid, isophthalic acid, terephthalic acid, tetrahydrophthalic acid, hexahydrophthalic acid, cyclohexanedicarboxylic acid, adipic acid, azelaic acid, sebacic acid, glutaric acid, tetrachlorophthalic acid, maleic acid, fumaric acid, itaconic acid, malonic acid, suberic acid, 2-methylsuccinic acid, 3,3-diethylglutaric acid and/or 2,2-dimethylsuccinic acid. The corresponding anhydrides can also be used as an acid source.

Where the average functionality of the polyol to be esterified is > than 2, it is also possible, additionally, to use monocarboxylic acids, as well, such as benzoic acid and hexanecarboxylic acid.

Preferred acids are aliphatic or aromatic acids of the aforementioned kind. Particular preference is given to adipic acid, isophthalic acid and phthalic acid.

Hydroxycarboxylic acids, which can be used as reaction participants as well when preparing a polyester polyol with terminal hydroxyl groups, are, for example, hydroxycaproic acid, hydroxybutyric acid, hydroxydecanoic acid, hydroxystearic acid and the like. Suitable lactones are caprolactone, butyrolactone and homologues. Caprolactone is preferred.

It is likewise possible to use polycarbonates containing hydroxyl groups, preferably polycarbonate diols, having number-average molecular weights $M_n$ of 400 to 8000 g/mol, preferably 600 to 3000 g/mol. They are obtainable by reaction of carbonic acid derivatives, such as diphenyl carbonate, dimethyl carbonate or phosgene, with polyols, preferably diols.

Examples of such diols are ethylene glycol, 1,2- and 1,3-propanediol, 1,3- and 1,4-butanediol, 1,6-hexanediol, 1,8-octanediol, neopentyl glycol, 1,4-bishydroxymethylcyclohexane, 2-methyl-1,3-propanediol, 2,2,4-trimethylpentane-1,3-diol, dipropylene glycol, polypropylene glycols, dibutylene glycol, polybutylene glycols, bisphenol A and lactone-modified diols of the aforementioned kind.

For prepolymer synthesis it is preferred to use polyether polyols of the aforementioned kind.

For the preparation of the prepolymer the compounds of component A1) are reacted with those of component A2) at an NCO/OH ratio of preferably 4:1 to 20:1, more preferably 8:1, and then the fraction of unreacted compounds of component A1) is separated off by means of appropriate methods. Typically for this purpose thin-film distillation is used, giving low-residual-monomer products having residual monomer contents of less than 1%, preferably less than 0.5% and very preferably less than 0.1% by weight.

Optionally it is possible, during or after the preparation, to add stabilizers such as benzoyl chloride, isophthaloyl chloride, dibutyl phosphate, 3-chloropropionic acid or methyl tosylate.

The reaction temperature is 20 to 120° C., preferably 60 to 100° C.

Preferably in formula (I):

R$_1$ and R$_2$ are identical or different, optionally branched or cyclic, organic radicals having 1 to 20, preferably 1 to 10, carbon atoms and containing no Zerewitinoff-active hydrogen, n is an integer from 2 to 4 and X is an n-valent, optionally branched or cyclic, organic radical having 2 to 20, preferably 5 to 10, carbon atoms and is obtained by removing the primary amino groups of an n-functional primary amine.

The amino-functional polyaspartic esters B1) are prepared in a known way by reaction of the corresponding primary, at least difunctional amines X(NH$_2$)$_n$ with maleic or fumaric esters of the general formula

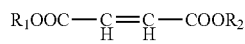

Preferred maleic or fumaric esters are dimethyl maleate, diethyl maleate, dibutyl maleate and the corresponding fumaric esters.

Preferred primary, at least difunctional amines X(NH$_2$)$_n$ are ethylenediamine, 1,2-diaminopropane, 1,4-diaminobutane, 1,3-diaminopentane, 1,5-diaminopentane, 2-methyl-1,5-diaminopentane, 1,6-diaminohexane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diamino-dicyclohexylmethane, 3,3'-dimethyl-4,4'-diaminodicyclohexylmethane, 2,4,4'-triamino-5-methyl-dicyclohexylmethane and polyetheramines having aliphatically attached primary amino groups, with a number-average molecular weight M$_n$ of 148 to 6000 g/mol.

Particularly preferred primary, at least difunctional amines are 1,3-diaminopentane, 1,5-diaminopentane, 2-methyl-1,5-diaminopentane, 1,6-diaminohexane, 1,13-diamino-4,7,10-trioxatridecane. 2-Methyl-1,5-diaminopentane is especially preferred.

Preferably R$_1$ and R$_2$ independently of one another are C$_1$ to C$_{10}$ alkyl radicals, more preferably methyl or ethyl radicals.

In one preferred embodiment of the invention R$_1$=R$_2$=ethyl, with X being based on 2-methyl-1,5-diaminopentane as the n-functional amine.

Preferably n in formula (I), for the description of the functionality of the n-functional amine, is an integer from 2 to 6, more preferably 2 to 4.

The preparation of the amino-functional aspartic esters B1) from the stated starting materials is accomplished in accordance with DE-A 69 311 633 preferably within the temperature range from 0 to 100° C., the starting materials being employed in proportions such that for each primary amino group there is at least one, preferably precisely one, olefinic double bond, and, after the reaction, any starting materials used in excess can be separated off by distillation. The reaction may take place in bulk or in the presence of suitable solvents such as methanol, ethanol, propanol or dioxane or mixtures of such solvents.

The organic liquid fillers used in B2) are preferably non-cytotoxic when their cyctotoxicity is measured in accordance with ISO 10993.

As organic fillers it is possible for example to use liquid polyethylene glycols such as PEG 200 to PEG 600, their monoalkyl and/or dialkyl ethers such as PEG 500 dimethyl ether, liquid polyether polyols and polyester polyols, liquid polyesters such as Ultramoll (Lanxess AG, Leverkusen, DE) and also glycerol and its liquid derivatives such as triacetin (Lanxess AG, Leverkusen, DE), for example.

The organic fillers of component B2) are preferably hydroxyl- or amino-functional compounds, preferably purely hydroxyl-functional compounds. Preferred purely hydroxyl-functional compounds are polyether polyols and/or polyester polyols, more preferably polyether polyols.

The preferred organic fillers of component B2) preferably possess average OH functionalities of 1.5 to 3, more preferably 1.8 to 2.2, very preferably 2.0.

The preferred organic fillers of component B2) preferably possess repeating units derived from ethylene oxide.

The viscosity of the organic fillers of component B2) is preferably 50 to 4000 mPas at 23° C. as measured to DIN 53019.

In one preferred embodiment of the invention polyethylene glycols are used as organic fillers of component B2). They preferably have a number-average molecular weight of 100 to 1000 g/mol, more preferably 200 to 400 g/mol.

The weight ratio of B1) to B2) is 1:0 to 1:20, preferably 1:0 to 1:12.

The weight ratio of component B2, based on the total amount of the mixture of B1, B2 and A, is situated in the range from 0 to 100%, preferably 0 to 60%.

In order further to reduce the average equivalent weight of the compounds used in total for prepolymer crosslinking, based on the NCO-reactive groups, it is also possible, in addition to the compounds used in B1) and B2), to prepare the amino- or hydroxyl-functional reaction products of isocyanate-functional prepolymers with aspartic esters and/or organic fillers B2), where the latter are amino- or hydroxyl-functional, in a separate preliminary reaction and then to use them as a relatively high molecular weight curing component C).

In the pre-extension it is preferred to use ratios of isocyanate-reactive groups to isocyanate groups of 50:1 to 1.5:1, more preferably 15:1 to 4:1.

The isocyanate-functional prepolymer to be used for this purpose may correspond to that of component A) or else, alternatively, may be constructed of the components listed as possible constituents of the isocyanate-functional prepolymers in the context of this specification.

An advantage of this modification by pre-extension is that the equivalent weight and equivalent volume of the curing component can be modified within clear limits. As a result, it is possible to carry out application using commercially available 2-chamber metering systems, to give an adhesive system which, with existing proportions of the chamber volumes, can be adjusted to the desired ratio of NCO-reactive groups to NCO groups.

If necessary it is possible to colour one of the two components.

The formulations essential to the invention are obtained by mixing the prepolymer with the curing component B) and/or C). In component B) and/or C) there may also be a biologically active component D). The ratio of NCO-reactive NH groups to free NCO groups is preferably 1:1.5 to 1:1, more preferably 1:1.

Immediately after the mixing of the individual components with one another, the formulations essential to the invention possess a shear viscosity at 23° C. of preferably 1000 to 10 000 mPas, more preferably 2000 to 8000 mPas and very preferably 2500 to 5000 mPas.

The rate at 23° C. until complete crosslinking and curing of the adhesive is achieved is typically 30 s to 10 min, preferably 1 min to 8 min.

The formulations essential to the invention can be applied for staunching the loss of blood and tissue fluids and also for sealing leaks in the human or animal body, and also as a tissue adhesive, preference being given to their in vivo application, for example, for emergency treatment in the case of polytrauma after accidents or operations.

EXAMPLES

Unless indicated otherwise, all percentages are by weight. PEG=polyethylene glycol Example 1 (Prepolymer A)

465 g of HDI and 2.35 g of benzoyl chloride were charged to a 1 l four-necked flask. Over the course of 2 h at 80° C. 931.8 g of a polyether having an ethylene oxide content of 71% and a propylene oxide content of 29% (based in each case on the total alkylene oxide content), prepared starting from TMP (3-functional), were added, with subsequent stirring for 1 h. Subsequently the excess HDI was removed by thin-film distillation at 130° C. and 0.1 torr. This gave 980 g (71%) of the prepolymer, with an NCO content of 2.53%. The residual monomer content was <0.03% HDI.

Example 2 (Aspartate B)

Under a nitrogen atmosphere 2 mol of diethyl maleate were slowly admixed dropwise with 1 mol of 2-methyl-1,5-diaminopentane, at a rate such that the reaction temperature did not exceed 60° C. Subsequently the mixture was heated to 60° C. until diethyl maleate was no longer detectable in the reaction mixture. The product was purified by distillation.

Example 3 (Application of the Formulations Essential to the Invention for Staunching Severe Bleeding and Sealing Leaks)

The formulations essential to the invention were applied by means of a commercial two-chamber applicator with static mixer. One chamber contained a mixture of 0.45 g of PEG 200 and 0.55 g of aspartate B. The second chamber contained 4 g of prepolymer A. Pressing down on the ram resulted in mixing of the two components.

In vivo experiments on haemostasis—animal model: rat

The experiment was carried out with a Wistar rat weighing 350 grams. Anaesthesia was induced with diethyl ether and subsequently, intraperitoneally, using ketamine/xylazine. Subsequently the trachea was intubated with a 14-gauge venous catheter. Ventilation was carried out with an air/oxygen mixture (FiO2=0.5). The rat was fixed to a heated support. Preparation for surgery was carried out aseptically and with local infiltration of lidocaine.

The abdomen was opened up by means of anterior longitudinal and transverse abdominal section, providing wide access to the liver and to the spleen.

Example 3a—Diffuse Bleeding

The surface of the liver was injured using sandpaper, producing diffuse bleeding. The formulation essential to the invention was applied to the surface of the liver. After about 2 minutes the film had cured and had staunched the bleeding of the liver surface.

Example 3b—Liver Resection

The tip of the left lobe of the liver was removed. This produced a cut area of approximately 1 cm², running transversely through the hepatic tissue, with severe bleeding. The formulation essential to the invention was applied, and staunched the bleeding within 2 minutes.

Example 3c—Pulmonary Aspiration

The rib cage was opened by medial sternotomy and widened with a right-lateral thoracotomy. The tip of the middle lobe of the right-hand lung was cut off, producing a wound area approximately 1 cm² in size. This resulted in strong venous and also strong arterial bleeding. Moreover, a medium-sized bronchus had been severed, resulting in an air leak. The tissue adhesive was applied to the wound area of the lung, and immediately staunched the venous and the arterial bleeding. With regard to the air leak, a large air bubble formed in the adhesive and burst, and there continued to be a fistula of air. After about 1 minute a drop of the adhesive was applied again to the air leak and pressed down firmly using a plastic spatula. This sealed the air leak.

After 3 minutes in all the film was cured and had successfully staunched the bleeds and sealed the air leak.

Example 3d—Aspiration of the Ascending Aorta

The ascending aorta was exposed and prepared. The ascending aorta was aspirated generously with a 0.5 mm thick needle, producing a squirting bleed. The formulation essential to the invention was applied to the bleed and pressed gently onto the hole using a plastic spatula. Bleeding came to a halt within 2 minutes.

In vivo experiments on haemostasis—animal model: pig

The experiment was carried out on a female 30 kg domesticated pig under inhalative mask anaesthesia. Incision of the skin was carried out ventrally to the sternocleidomastoid muscle, on the left-hand side. The carotid aorta was exposed in the region of the bulb. The carotid aorta is found to have a diameter of approximately 5-6 mm.

Example 3e—Minor Arterial Bleeding

Using a scalpel, the carotid artery was opened in the region of the bulb by careful preparation in such a way that there was a minor squirting bleed from the artery. After brief initial rinsing of the mixing canula, approximately 4 ml of the formulation essential to the invention were applied to the source of the bleeding, and compressed by means of compression through surrounding tissue, in particular through the sternocleidomastoid muscle. The bleeding halted after about 1½ min. The surrounding tissue had been bonded to the carotid artery. A pulse could be felt on the carotid artery, distal to the site of the incision.

Example 3f—Severe Arterial Bleeding

Using vessel scissors, the carotid artery was opened over half the circumference. In the course of this operation, a severe squirting arterial bleed developed. 5 ml of the formulation essential to the invention were applied to the site of the bleed and compressed with the surrounding tissue over about 2 min. The bleeding came to a halt after 2 minutes.

Example 3g—Venous Bleeding

The right aural vein was opened using a scalpel over a length of approximately 10 mm, resulting in a severe bleed.

The formulation essential to the invention was applied without compression. The bleed came to a halt after about 1 minute.

The invention claimed is:

1. A formulation for staunching the loss of blood (haemostatic) or tissue fluids comprising:
   A) an isocyanate-functional prepolymer obtained from
      A1) an aliphatic isocyanate and
      A2) a polyol component having a number-average molecular weight of greater than or equal to 400 g/mol and an average OH functionality of 2 to 6,
   B) a curing component comprising
      B1) an amino-functional aspartic ester of the general formula (I)

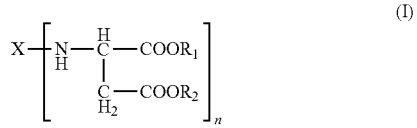

where
   X is an organic radical obtained by removing the primary amino groups from 2-methyl 1,5-diaminopentane;
   $R_1$ and $R_2$ are ethyl and
   n is 2;
   B2) optionally, organic fillers which have a viscosity as measured to DIN 53019 at 23° C. in the range from 10 to 6000 mPas,
   and
   C) optionally, reaction products of isocyanate-functional prepolymers as defined for component A) with aspartic esters as per component B1) and/or organic fillers as per component B2).

2. The formulation according to claim 1, wherein the curing component further comprises organic fillers which have a viscosity as measured to DIN 53019 at 23° C. in the range of from 10 to 6000 mPas.

3. The formulation according to claim 2, wherein the formulation further comprises reaction products of the isocyanate-functional prepolymer with the organic fillers.

4. The formulation according to claim 1, wherein the formulation further comprises reaction products of the isocyanate-functional prepolymer with the amino-functional aspartic ester.

5. The formulation according to claim 4, wherein the formulation further comprises reaction products of the isocyanate-functional prepolymer with organic fillers.

6. The formulation according to claim 1, wherein the curing component further comprises organic fillers which have a viscosity as measured to DIN 53019 at 23° C. in the range of from 10 to 6000 mPas and wherein the formulation further comprises reaction products of the isocyanate-functional prepolymer with the amino-functional aspartic ester and the organic fillers.

7. The formulation according to claim 1, wherein the polyol component has a number-average molecular weight of 4000 to 8500 g/mol.

8. The formulation according to claim 1, wherein the polyol component comprises a polyalkylene oxide polyether.

9. The formulation according to claim 8, wherein the polyalkylene oxide polyether contains from 60% to 90% of ethylene oxide-based units, based on the total amount of alkylene oxide units.

10. The formulation according to claim 2, wherein the organic fillers comprise polyether polyols.

11. The formulation according to claim 1, wherein the formulation is curable for a period of time from 30 seconds to 10 minutes.

12. The formulation according to claim 1, wherein the formulation is curable for a period of time from 30 seconds to 2 minutes.

* * * * *